United States Patent
Ikawa

(10) Patent No.: US 10,314,299 B2
(45) Date of Patent: Jun. 11, 2019

(54) INSECT TRAP

(71) Applicant: Shikoku Cage Co., Ltd., Ehime (JP)

(72) Inventor: Shigeki Ikawa, Ehime (JP)

(73) Assignee: SHIKOKU CAGE CO., LTD., Ehime (JP)

( * ) Notice: Subject to any disclaimer, the term of this patent is extended or adjusted under 35 U.S.C. 154(b) by 179 days.

(21) Appl. No.: 15/533,258

(22) PCT Filed: Oct. 16, 2015

(86) PCT No.: PCT/JP2015/079361
§ 371 (c)(1),
(2) Date: Jun. 5, 2017

(87) PCT Pub. No.: WO2016/088458
PCT Pub. Date: Jun. 9, 2016

(65) Prior Publication Data
US 2017/0339939 A1    Nov. 30, 2017

(30) Foreign Application Priority Data
Dec. 5, 2014    (JP) .................... 2014-261226

(51) Int. Cl.
*A01M 1/10* (2006.01)
*F24V 30/00* (2018.01)
(Continued)

(52) U.S. Cl.
CPC ............ *A01M 1/103* (2013.01); *A01M 1/023* (2013.01); *A01M 1/10* (2013.01); *A01M 1/2011* (2013.01);
(Continued)

(58) Field of Classification Search
CPC .......... A01M 1/103; A01M 1/023; A01M 1/10
(Continued)

(56) References Cited

U.S. PATENT DOCUMENTS 4,395,842 A * 8/1983 Margulies ............... A01M 1/02
43/114
5,119,586 A * 6/1992 Townsend ............. A01M 1/023
43/114
(Continued)

FOREIGN PATENT DOCUMENTS

EP    0925717 A1    6/1999
JP    S54101182 U    7/1979
(Continued)

OTHER PUBLICATIONS

Extended European Search Report dated Jun. 11, 2018 for corresponding European Patent Application No. 15865876.5.
(Continued)

*Primary Examiner* — Christopher P Ellis
(74) *Attorney, Agent, or Firm* — David D. Brush; Westman, Champlin & Koehler, P.A.

(57) ABSTRACT

An insect trap includes an exothermic body, and a layered body. The exothermic body is configured to include exothermic powder enclosed in an inner bag that is air permeable; the exothermic powder contains iron powder that releases heat when oxidized. The layered body is configured with layers of plate-like elements and includes gaps as a pathway of entry for an insect pest. A housing space to house the exothermic body is arranged inside the layered body. The layered body and the inner bag are made of a biodegradable raw material.

8 Claims, 6 Drawing Sheets

(51) Int. Cl.
*A01M 1/02* (2006.01)
*A01M 1/20* (2006.01)
*A01N 25/08* (2006.01)
*A01N 27/00* (2006.01)
*A01N 59/14* (2006.01)

(52) U.S. Cl.
CPC ............ *A01N 25/08* (2013.01); *A01N 27/00* (2013.01); *A01N 59/14* (2013.01); *F24V 30/00* (2018.05)

(58) Field of Classification Search
USPC .......................................................... 43/107
See application file for complete search history.

(56) References Cited

U.S. PATENT DOCUMENTS

| | | | |
|---|---|---|---|
| 5,937,571 A * | 8/1999 | Megargle | A01M 1/026 43/124 |
| 2003/0019440 A1 | 1/2003 | Takacs et al. | |
| 2006/0017577 A1 | 1/2006 | Broussard | |
| 2010/0260491 A1 | 10/2010 | Pitz et al. | |
| 2010/0310499 A1 | 12/2010 | Skelton et al. | |
| 2011/0138678 A1 * | 6/2011 | Smith | A01M 1/023 43/107 |
| 2012/0285076 A1 * | 11/2012 | Banfield | A01M 1/026 43/123 |
| 2012/0291337 A1 * | 11/2012 | Curcio | A01M 1/14 43/114 |
| 2015/0223442 A1 | 8/2015 | Yamauchi et al. | |
| 2018/0027794 A1 * | 2/2018 | Hortel | A01M 1/2011 |

FOREIGN PATENT DOCUMENTS

| | | |
|---|---|---|
| JP | H10108607 A | 4/1998 |
| JP | 2002293683 A | 10/2002 |
| JP | 2004538286 A | 12/2004 |
| JP | 2011509987 A | 3/2011 |
| JP | 2014117274 A | 6/2014 |
| JP | WO2014030353 A1 | 7/2016 |
| WO | 9931974 A1 | 7/1999 |
| WO | 2007016705 A2 | 2/2007 |
| WO | 2012147421 A1 | 11/2012 |

OTHER PUBLICATIONS

International Preliminary Report on Patentability and English translation of the Written Opinion dated Jan. 19, 2016 for corresponding International Application No. PCT/JP2015/079361, filed Oct. 16, 2015.

International Search Report dated Jan. 7, 2016 for corresponding International Application No. PCT/JP2015/079361, filed Oct. 16, 2015.

Sayaka et al., "Dermanyssus Gallinae Countermeasures Using with Cardboard", Tochigi Prefecture FY2012 Business Outline, (online) Sep. 13, 2013, retrieval date Jan. 5, 2016. Reference explained in ISA/237 of PCT/JP2015/079361, filed Oct. 16, 2015.

Odaka, Makiko et al., "Development of a trap for Dermanyssus Gallinaes", Japanese Journal of Zootechnical Science, Jun. 21, 2014, vol. 85 (2), pp. 187-192. English summary included.

* cited by examiner

INSECT TRAP

CROSS-REFERENCE TO RELATED APPLICATION

This Application is a 371 National Stage Application of International Application No. PCT/JP2015/079361, filed Oct. 16, 2015, published as WO 2016/088458 A1, on Jun. 9, 2016, not in English, which is based on and claims the benefit of Japanese Patent Application No. 2014-261226, filed on Dec. 5, 2014 with the Japan Patent Office, the contents of which are hereby incorporated by reference in their entireties.

TECHNICAL FIELD

The present disclosure relates to an insect trap.

BACKGROUND ART

Mites such as red mites and northern fowl mites are insect pests that feed on blood of chickens, for example. Due to anemia and stress caused by hematophagous behavior of these insect pests, there are problems of decreasing intake of fodder and decreasing egg laying rate in the chicken industry. To cope with these problems, high-temperature steam is sprayed inside chicken houses, or, agents such as insecticides are dispersed. Patent Document 1 discloses an insect trap that can capture insect pests such as ticks and mites. Insect pests such as ticks and mites can be captured if such an insect trap is used.

PRIOR ART DOCUMENTS

Patent Documents

Patent Document 1: Japanese Unexamined Patent Application Publication No. H10-108607

SUMMARY OF THE INVENTION

Problems to be Solved by the Invention

In addition to ticks and mites, other insects such as ants and cockroaches are also targets of the aforementioned insect trap disclosed in Patent Document 1. The insect trap is accordingly configured to allow entry of large insects. Specifically, the insect trap is provided with floor boards; a sufficiently large space is secured vertically between each of these floor boards. Materials such as wall materials are also provided to support these floor boards. Accordingly, production of such an insect trap requires parts cut out into complicated shapes, and the number of parts overly grows. This results in a problem of troublesome production of the insect trap. In addition, Patent Document 1 does not particularly explain how the insect trap is disposed of after use.

One aspect of the present disclosure is to provide an insect trap that can be easily produced. Another aspect of the present disclosure is to provide an insect trap that is easily disposed of after use.

Means for Solving the Problems

One aspect of the present disclosure is an insect trap that comprises an exothermic body, and a layered body. The exothermic body is configured to comprise exothermic powder enclosed in an inner bag that is air permeable, wherein the exothermic powder contains iron powder that releases heat when oxidized. The layered body is configured with layers of plate-like elements. The layered body comprises gaps as pathways of entry for an insect pest. A housing space to house the exothermic body is arranged inside the layered body. The layered body and the inner bag are made of a biodegradable raw material.

Such an insect trap can be produced by layering the plate-like elements. Necessary parts to produce such an insect trap are therefore easily simplified in shape and reduced in number compared with those of, for example, insect traps that have a complex structure where floor boards are arranged with a space between one another and supported by wall surfaces. Structure of such an insect trap can therefore be configured for simple and easy production.

In addition, the layered body and the inner bag of such an insect trap comprise a biodegradable raw material, in other words, a raw material degraded by microorganisms. Such an insect trap can therefore be disposed of, for example, by a method to appropriately crush and bury them under soil without requesting industrial waste contractor for disposal as an industrial waste. Particularly in poultry farming, chicken excreta are processed into manure in chicken manure treatment facilities since a large volume of chicken excreta is collected from chicken houses. In the chicken manure treatment facilities, chicken excreta are mixed to accelerate fermentation and made into manure by a mixer.

When such a mixer is used, the insect trap can be dropped into the mixer and crushed into fragments by the mixer; at the same time, the fragments can be mixed with chicken excreta to accelerate biodegradation of the fragments. Since the exothermic powder included in the insect trap contains iron powder, iron content of the manure increases when the fragments of the insect trap are mixed with chicken excreta, compared with when manure is made of chicken excreta alone. Used insect traps can thus be utilized to produce manure that is suitable for application on agricultural crops requiring iron. Furthermore, since iron absorbs causative substances of foul odor such as ammonia, hydrogen sulfide, and trimethylamine, foul odor generated during processing of chicken excreta can be reduced.

EXPLANATION OF REFERENCE NUMERALS

1 . . . insect trap, 2, 3, 4 . . . cardboard sheet, 5 . . . exothermic body, 5A . . . inner bag, 5B . . . powder, 6 . . . outer bag, 7 . . . hide glue, 8 . . . layered body, 10 . . . insect trap, 12, 13, 14 . . . cardboard sheet, 31 . . . insect trap, 32, 33, 34, 35, 36 . . . cardboard sheet, 37 . . . layered body, 50 . . . opening, 51 . . . insect trap, 52, 53, 54 . . . cardboard sheet, 58 . . . layered body

MODE FOR CARRYING OUT THE INVENTION

Hereinafter, embodiments to which the present disclosure is applied are explained with reference to the drawings.

1. First Embodiment

[1-1. Configuration]

Figure 1:
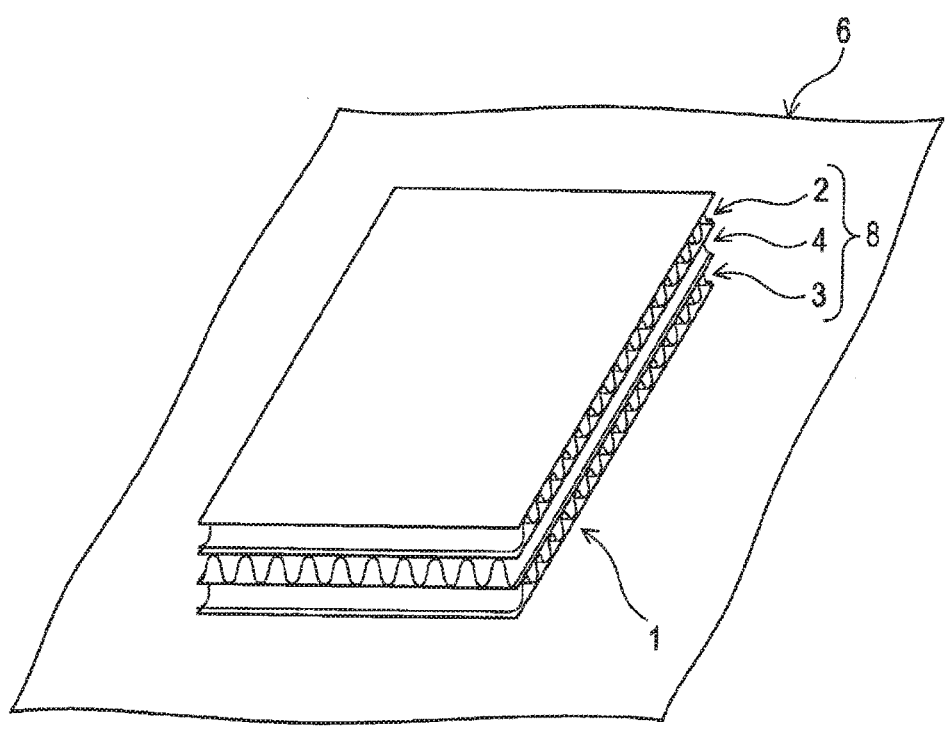
FIG. 1 is a perspective view showing an insect trap according to the first embodiment.
Figure 2:
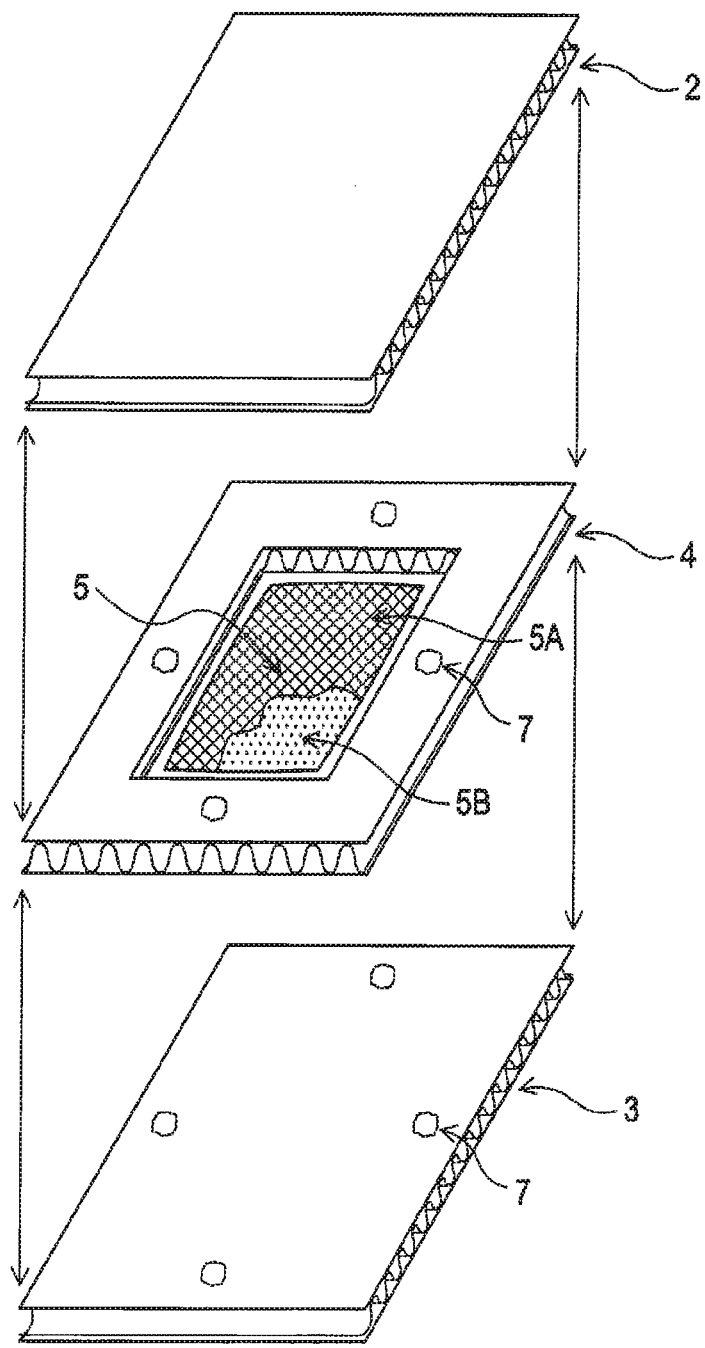
FIG. 2 is an exploded view showing an inner structure of the insect trap according to the first embodiment.

An insect trap 1 shown in FIG. 1 and FIG. 2 comprises a layered body 8, and an exothermic body 5 arranged inside the layered body 8. The insect trap 1 is enclosed in an airtight outer bag 6.

The layered body 8 has a layered structure comprising three rectangle cardboard sheets 2, 3, and 4 (which correspond to one example of plate-like elements in the present specification). The cardboard sheets 2, 3, and 4 are those typically known and configured with a corrugated core material, and two liners that are respectively bonded to both sides of the core material to place the core interposed between the two liners. The cardboard sheets 2, 3, and 4 may be those configured with a core material, and one liner (so-called single-face cardboards).

The cardboard sheets 2, 3, and 4 selected for use are high in biodegradability. Specifically, the cardboard sheets 2, 3, and 4 made from 100 percent recycled paper are used. Use of such cardboard sheets 2, 3, and 4 increases biodegradability of the cardboard sheets 2, 3, and 4 compared with a case of using cardboards with a higher pulp content ratio. In addition, the cardboard sheets 2, 3, and 4 whose basis weight is 100 g are used. Basis weight is a unit representing a weight of one square meter of paper. Use of such cardboard sheets 2, 3, and 4 increases biodegradability of the cardboard sheets 2, 3, and 4 compared with a case of using cardboards with a greater (heavier) basis weight.

The cardboard sheet 4, situated in the middle of the three cardboard sheets 2, 3, and 4, has its central area cut out to form a rectangle opening. A housing space to house the exothermic body 5 is provided by interposing this cardboard sheet 4 between the two cardboard sheets 2, and 3.

The cardboard sheets 2, 3, and 4 are bonded with hide glue 7. As shown in FIG. 2, the hide glue 7 is applied on four locations between the cardboard sheets 2, and 4. The hide glue 7 is also applied on four locations between the cardboard sheets 3, and 4. The core material and the liners of each of the cardboard sheets 2, 3, and 4 form gaps that extend parallel to one another. Entries to the gaps are open to the outside at a seemingly corrugated end surface of each of the cardboard sheets 2, 3, and 4. The cardboard sheets 2, and 4, situated next to one another in the layered body 8, each have a direction of extension of gaps oriented to be orthogonal to each other when viewed from a layered direction of the cardboard sheets 2, and 4. The cardboard sheets 3, and 4, likewise next to one another, each have a direction of extension of gaps oriented to be orthogonal to each other when viewed from a layered direction of the cardboard sheets 3, and 4.

The cardboard sheets 2, 3, and 4 carry boric acid that is toxic to insect pests. More specifically, a solution of the boric acid is spray-applied to the sheets and then dried; the boric acid is therefore carried mainly on surfaces of the cardboard sheets 2, 3, and 4 in the present embodiment. The method of having the boric acid carried on the cardboard sheets 2, 3, and 4 is not limited to the aforementioned method. Instead of spray-applying the solution of the boric acid to the cardboard sheets 2, 3, and 4, the cardboard sheets 2, 3, and 4 may also be immersed in the solution of the boric acid to allow the solution of the boric acid to permeate the cardboard sheets 2, 3, and 4. Alternatively, the solution of the boric acid may also be applied on the cardboard sheets 2, 3, and 4 with a tool such as a brush.

The cardboard sheets 2, 3, and 4 also carry an attractant that includes limonene as an attractant for insect pests. Specifically, a limonene-containing citrus essential oil such as orange oil, lemon oil, and lime oil is applied on the cardboard sheets 2, 3, and 4 in the present embodiment. It is preferable to apply the citrus essential oil on a location near the exothermic body 5 so that dispersion of limonene can be promoted. In the present embodiment, one drop of the aforementioned attractant (citrus essential oil) is applied on each one of four inner surfaces that shape the rectangle opening formed on the cardboard sheet 4 (total of 4 drops).

As shown in FIG. 2, the exothermic body 5 comprises an inner bag 5A that is air permeable, and exothermic powder 5B enclosed in the inner bag 5A. In FIG. 2, the exothermic powder 5B inside the inner bag 5A is shown partially in a cutaway section of the inner bag 5A. The inner bag 5A is made of a film material whose base material is cellophane. The exothermic powder 5B contains reduced iron powder that releases heat when oxidized.

When in use, the insect trap 1 configured as described above is placed at a required location, for example, inside a chicken house with its outer bag 6 opened. After the outer bag 6 is opened, the exothermic body 5 is exposed to air, which causes the reduced iron powder contained in the exothermic powder 5B to be oxidized by oxygen in the air and thus causes the exothermic body 5 to release heat. Composition of the exothermic powder 5B is adjusted with respect to, for example, compounding ratio of each component and contained amount of the reduced iron powder, so as to maintain temperature of the heat from 40 to 45° C. for 24 hours or longer.

As the exothermic body 5 releases heat, temperature inside or around the insect trap 1 increases; those insect pests that favor such an environment gather to the insect trap 1. Acaris such as red mites and northern fowl mites enter into the cardboard sheets 2, 3, and 4 from the gaps at the end surfaces of the cardboard sheets 2, 3, and 4 since they favor narrow gaps and dark environments. There are also gaps between the cardboard sheet 2 and the cardboard sheet 4, and between the cardboard sheet 3 and the cardboard sheet 4; insect pests also enter into these gaps. In the present embodiment, components included in limonene and hide glue are also diffused to the outside of the insect trap 1 as the exothermic body 5 releases heat; thus those insect pests that favor such components are likely to gather.

The insect trap 1 is collected and disposed of after being installed inside a chicken house for half a day to five days, for example. Insect pests inside the chicken house are thereby expelled. Although the collected insect trap 1 can be disposed of or incinerated, it can also be used as feedstock for chicken manure. To be more specific, chicken excreta is mixed in a mixer to accelerate its fermentation and made into manure when processing the chicken excreta into manure in a chicken manure treatment facility. Accordingly, the collected insect trap 1 is fed into the mixer to be crushed into fragments by the mixer, and the fragments are mixed with the chicken excreta and made into manure.

Fragments of the cardboard sheets 2, 3, and 4 and the inner bag 5A are contained in a mixture that is made into manure as described above. Since all of these fragments are made from materials that are high in biodegradability, these fragments can be biologically decomposed and degraded into soil while being processed into manure or while in the soil after applied as fertilizer. The exothermic powder 5B is also degraded into soil by being directly mixed into the soil. Particularly, the oxidized iron powder contained in the exothermic powder 5B becomes a fertilizer for plants that favor iron.

[1-2. Performance Assessment of Insect Trap]

Performance of the insect trap 1 explained in the present embodiment was assessed by the following method.

The insect trap 1 was installed in a chicken house to test how many Acaris, such as red mites, could be captured. Specifically, three stories of racks to arrange cages for raising chickens were installed inside the chicken house; each rack carried a plurality of cages. The insect trap 1 was installed on each rack and collected after one or four days had passed to measure its weight; a captured amount of red mites was estimated based on increase in weight. One gram of the captured red mites was weighed and counted for the number of red mites included, which amounted to 16,200. Accordingly, one gram of the measured weight was converted to 16,200 red mites in the present embodiment.

For a purpose of comparison, an insect trap that only comprises cardboard sheets (hereinafter, referred to as a control insect trap) was prepared. The cardboard sheets used in the control insect trap were made of the same raw material and made in the same shape as the cardboard sheets 2, 3, and 4 of the insect trap 1 in the present embodiment. However, the control insect trap does not comprise an exothermic body 5. The control insect trap also does not carry boric acid and an attractant containing limonene. In addition, three cardboard sheets of the control insect trap are not bonded together with hide glue; the cardboard sheets are only layered on one another. Such a control insect trap was also installed inside the chicken house under the same conditions as the above-described insect trap 1; and the weight of the control insect trap was measured after the same number of days had passed. The results of these tests are shown in the following Tables 1 and 2.

TABLE 1

| Insect Trap 1 explained in the present embodiment | | | | |
|---|---|---|---|---|
| | Lower rack | Middle rack | Upper rack | Total |
| One-day installment (One trap per 16 chickens) | | | | |
| Collected Traps (trap) | 9 | 8 | 7 | 24 |
| Weight captured (g) | 4.72 | 4.59 | 5.10 | 14.41 |
| Amount captured (in number) | 76500 | 74400 | 82600 | 235500 |
| Red mites per sheet (in gram) | 0.52 | 0.57 | 0.73 | 0.60 |
| (in number) | 8500 | 9300 | 11800 | 9800 |
| Four-day installment (One trap per 16 chickens) | | | | |
| Collected Traps (trap) | 9 | 7 | 6 | 22 |
| Weight captured (g) | 14.94 | 11.19 | 28.63 | 57.76 |
| Amount captured (in number) | 242000 | 181300 | 463800 | 887100 |
| Red mites per sheet (in gram) | 1.66 | 1.60 | 4.77 | 2.63 |
| (in number) | 26900 | 25900 | 77300 | 43370 |

TABLE 2

| Control Insect Trap | | | | |
|---|---|---|---|---|
| | Lower rack | Middle rack | Upper rack | Total |
| One-day installment (One trap per 16 chickens) | | | | |
| Collected Traps (trap) | 9 | 7 | 8 | 24 |
| Weight captured (g) | 0.71 | 0.89 | 1.47 | 3.07 |
| Amount captured (in number) | 11500 | 14400 | 23800 | 49700 |
| Red mites per sheet (in gram) | 0.08 | 0.13 | 0.18 | 0.13 |
| (in number) | 1300 | 2100 | 3000 | 2100 |
| Four-day installment (One trap per 16 chickens) | | | | |
| Collected Traps (trap) | 8 | 8 | 8 | 24 |
| Weight captured (g) | 2.38 | 2.41 | 4.70 | 9.49 |
| Amount captured (in number) | 38600 | 39000 | 76100 | 153700 |
| Red mites per sheet (in gram) | 0.30 | 0.31 | 0.59 | 0.40 |
| (in number) | 4800 | 4900 | 9500 | 6400 |

According to the results shown above, it is seen that the insect trap 1 of the present embodiment can capture 4.7 times more red mites for one-day installment and 6.8 times more red mites for four-day installment than the control insect trap can.

[1-3. Effect]

Effects shown below can be obtained according to the aforementioned present embodiment.

(1a) The insect trap 1 of the present embodiment has a layered structure comprising the three cardboard sheets 2, 3, and 4. Therefore, the insect trap 1 can be easily made thinner than the aforementioned insect trap disclosed in Patent Document 1, and thus can be easily installed in a narrow installment spaces such as a space between cages arranged inside the chicken house and a space above and below the cages. Moreover, it is easy to keep the insect trap 1 before use since the insect trap 1 of the present embodiment is not as bulky as the insect trap disclosed in Patent Document 1.

(1b) In the insect trap 1 of the present embodiment, the cardboard sheets 2, 3, and 4 have a structure comprising the gaps that extend parallel to one another; the entries to the gaps are open at the end surface of each of the cardboard sheets 2, 3, and 4. According to such a configuration, the gaps of the cardboard sheets can be used to form a pathway of entry for the insect pest. The pathway of entry for the insect pest can therefore be easily formed compared with a case where the insect trap is configured with a material other than the cardboard sheets.

In the insect trap 1 of the present embodiment, the cardboard sheets 2, and 4 in the layered body 8 each have a direction of extension of gaps oriented to be orthogonal to each other when viewed from a layered direction of the cardboard sheets 2, and 4. It is likewise for the cardboard sheets 3, and 4. Accordingly, the insect trap 1 configured as above can capture insect pests that enter from four directions.

(1c) In the insect trap 1 of the present embodiment, the layered body 8 carries boric acid that is toxic to insect pests. Insect pests entering the insect trap 1 can therefore be killed.

(1d) In the insect trap 1 of the present embodiment, the adjoined cardboard sheets 2, 3, and 4 are bonded with the hide glue 7. The insect trap 1 can therefore be processed with chicken excreta to be made into manure in the chicken manure treatment facility, unlike a case where an adhesive made of a low-biodegradable synthetic resin is used.

Other than functioning as an adhesive, the hide glue 7 also works to attract insect pests. Accordingly, if the hide glue 7 is used as an adhesive, insect pests are more likely to be attracted and thus more insect pests can be captured than in a case where other adhesive is used.

(1e) In the insect trap 1 of the present embodiment, the layered body 8 carries an attractant that contains limonene. The insect trap 1 can therefore attract insect pests due to effect of limonene. Thus, the insect trap 1 can capture more insect pests than an insect trap that does not carry a limonene-containing attractant.

(1f) In the insect trap 1 of the present embodiment, the inner bag 5A is made of a film material whose base material is cellophane. The insect trap 1 can therefore be processed with chicken excreta to be made into manure in the chicken manure treatment facility, unlike a case where an inner bag made of a low-biodegradable material is used.

(1g) In the insect trap 1 of the present embodiment, the insect trap 1 is completely enclosed in an airtight outer bag 6. Thus, if the exothermic body 5 itself is not enclosed in an airtight bag, the exothermic body 5 does not release heat unless the outer bag 6 is opened. When using the insect trap 1, it is only required to open the outer bag 6 to cause the exothermic body 5 to release heat. Unlike a configuration where the exothermic body itself is enclosed in an airtight bag, it is not necessary to take the trouble to remove the exothermic body 5, enclosed in an airtight bag, from the layered body 8 to open the airtight bag. The insect trap 1 can therefore be initiated with easy operation.

2. Second Embodiment

Basic configurations of the second embodiment are the same as those of the first embodiment. Therefore, explanation is omitted with respect to common configurations, but is focused on differences. In the second embodiment, the same reference numerals as those of the first embodiment represent the same configurations, and therefore refer to the preceding explanations.

[2-1. Configuration]

Figure 3:
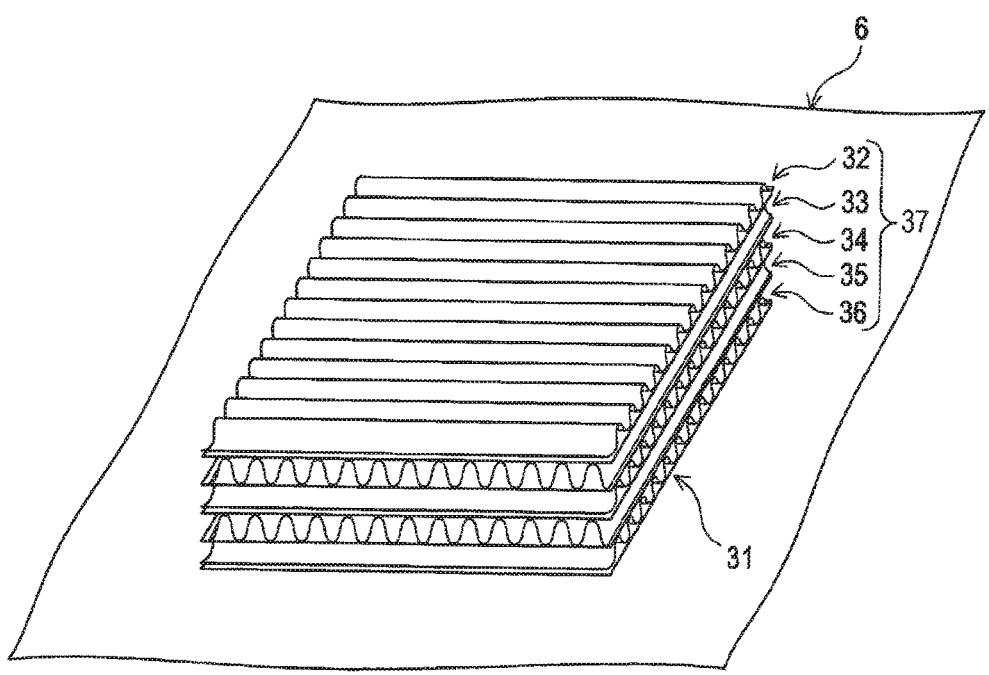
FIG. 3 is a perspective view showing an insect trap according to the second embodiment.
Figure 4:
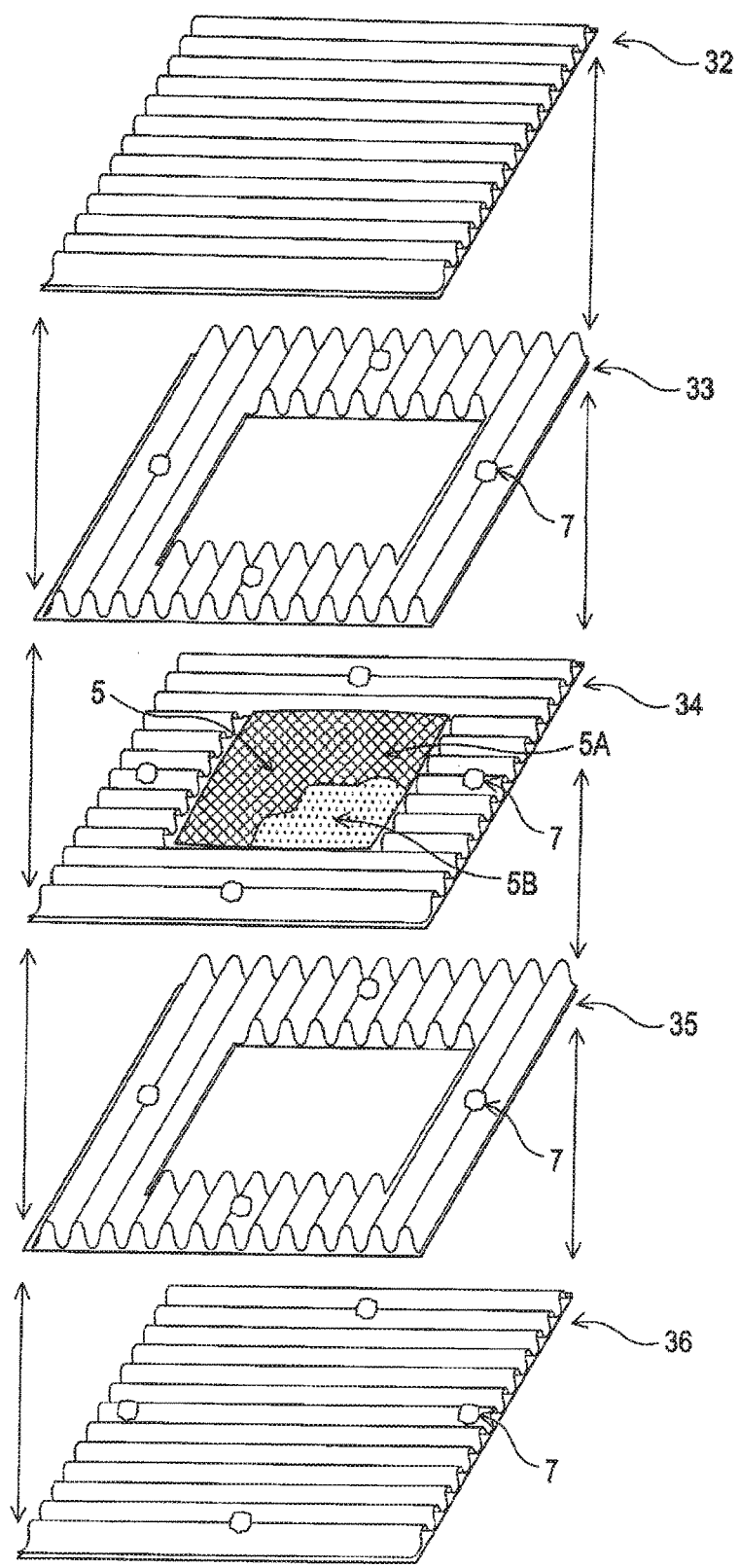
FIG. 4 is an exploded view showing an inner structure of the insect trap according to the second embodiment.

The insect trap 31 shown in FIG. 3 and FIG. 4 comprises the layered body 37, and an exothermic body 5 arranged inside the layered body 37.

The layered body 37 has a layered structure comprising five square cardboard sheets 32, 33, 34, 35, and 36.

Among the five cardboard sheets 32, 33, 34, 35, and 36, the cardboard sheets 33, 34, and 35, which are interposed between two cardboard sheets 32, and 36 situated as the most superficial layers of the layered body, each have their central area cut out to form a square opening. A housing space to house the exothermic body 5 is arranged by interposing these cardboard sheets 33, 34, and 35 between the two cardboard sheets 32, and 36.

[2-2. Effect]

(2a) The insect trap 31 of the second embodiment has a layered structure comprising the five cardboard sheets 32, 33, 34, 35, and 36. Therefore, the insect trap 31 comprises more open gaps as pathways of entry for the insect pests than the insect trap 1 of the first embodiment does. Accordingly, when such an insect trap 31 is used, insect pests can enter the insect trap 31 more easily than to enter those insect traps that are configured with a less number of layered cardboard sheets than the insect trap 31 is.

(2b) In the insect trap 31 of the second embodiment, a housing space for the exothermic body 5 is formed by cutting the three cardboard sheets 33, 34, and 35. The housing space in the insect trap 31 can therefore be more spacious than that of the insect trap 1 of the first embodiment. Accordingly, the insect trap 31 can house a larger exothermic body 5 than the exothermic body 5 housed in the insect trap 1, and have a longer heat-release duration than that of the insect trap 1.

3. Other Embodiments

Although the embodiments of the present disclosure have been explained above, the present disclosure can be embodied in various modes without being limited to the aforementioned embodiments.

(3a) As examples of the layered body, the aforementioned embodiments showed a case of layering the three cardboard sheets 2, 3, and 4, and a case of layering the five cardboard sheets 32, 33, 34, 35, and 36. Nevertheless, any number of cardboard sheets may be layered without limiting the number to three and five.

(3b) As examples of the biodegradable plate-like elements, the aforementioned embodiments showed the cardboard sheets 2, 3, and 4, and the cardboard sheets 32, 33, 34, 35, and 36. Nevertheless, the biodegradable plate-like elements are not limited to these cardboard sheets. For example, a material such as a biodegradable plastic may be used to make plate-like elements the same as or similar to the cardboard sheets. If plate-like elements other than the cardboard sheets are selected, it is still preferable to arrange gaps in the plate-like elements as pathways of entry for insect pests. Alternatively, the layered body may comprise a plate-like element that has no gaps arranged therein as long as the gaps are arranged between adjacently layered plate-like elements. Preferably, a size of a gap arranged in the layered body is 0.1 to 10 mm, in particular, 0.5 to 5 mm.

Figure 5:
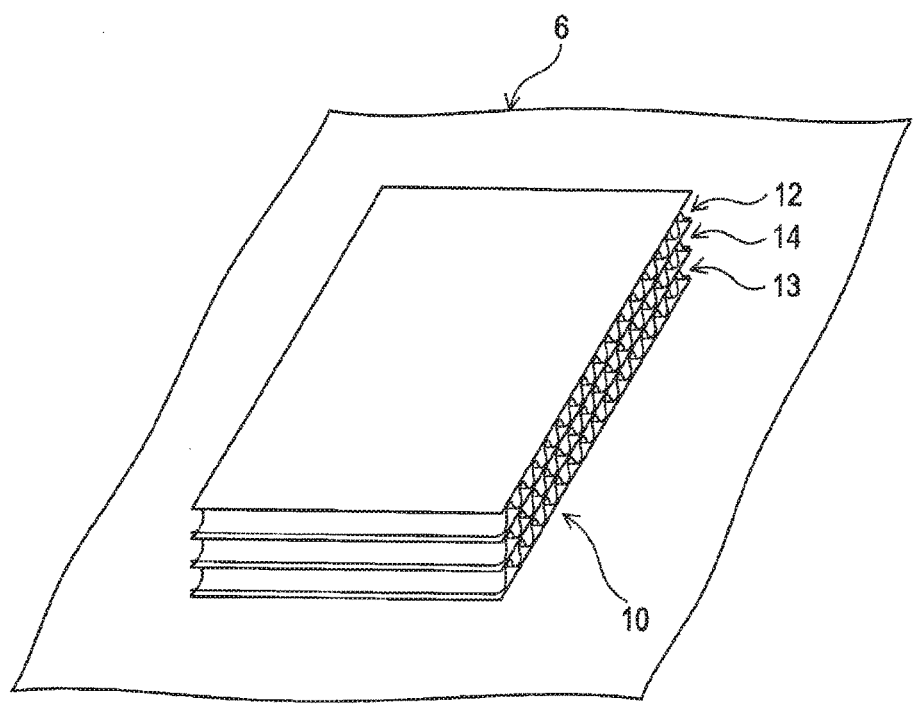
FIG. 5 is a perspective view showing an insect trap according to another embodiment.

(3c) As an example of the arrangement of the plate-like elements, the aforementioned first embodiment showed a case where the cardboard sheets 2, and 4, situated next to one another, each have a direction of extension of gaps oriented to be orthogonal to each other when viewed from a layered direction of the cardboard sheets 2, and 4. The first embodiment also showed a case where the cardboard sheets 3, and 4, likewise next to one another, each have a direction of extension of gaps oriented to be orthogonal to each other when viewed from a layered direction of the cardboard sheets 3, and 4. The plate-like elements are also likewise arranged in the aforementioned second embodiment. Nevertheless, the arrangement of the plate-like element is not limited to orthogonal direction arrangement. For example, as an insect trap 10 shown in FIG. 5, adjoining cardboard sheets 12, 13, and 14 may each have a direction of extension of gaps oriented to be parallel to one another when viewed from a layered direction of the cardboard sheets 12, 13, and 14.

(3d) As an example of the adhesive, the aforementioned embodiments showed cases where the hide glue 7 is used. Nevertheless, the adhesive is not limited to the hide glue 7 and may be made from a natural material. For example, an adhesive made from starch paste such as rice glue may be used.

(3e) As an example of the number of locations to apply the hide glue 7, the aforementioned embodiments showed cases where the hide glue 7 is applied on four locations on the cardboard sheets 2, 3, and 4, and on the cardboard sheets 32, 33, 34, 35, and 36. Nevertheless the number of locations to apply the hide glue 7 is not limited to those in the aforementioned cases. For example, the cardboard sheets may be bonded by applying the hide glue 7 on any one or more locations on the cardboard sheets. Alternatively, the cardboard sheets may be bonded by applying the hide glue thinly across the entire cardboard sheets.

As mentioned above, since the hide glue 7 has an effect of attracting the insect pests, the hide glue 7 may be used not as an adhesive, but as a mere attractant.

(3f) The aforementioned embodiments showed an example where the inner bag is made of a film material whose base material is cellophane. Nevertheless, a material to make the inner bag is not limited to the aforementioned material. The inner bag may be made of any material other than cellophane as long as the material is biodegradable. Although it is not mentioned in the aforementioned embodiments, the film material that makes the inner bag may be processed by a surface treatment (for example, coating treatment) on its base material using a material other than the base material to an extent not inhibiting the biodegradation of the inner bag. For example, when the inner bag is made of a film material whose base material is cellophane, a surface of the base material (cellophane) may be treated with a moisture-proof agent.

(3g) Although it is not particularly mentioned in the aforementioned embodiments, the cardboard sheets 2, 3, 4, 32, 33, 34, 35, and 36 may be colored or not colored. It is preferable to use black when coloring the cardboard sheets 2, 3, and 4.

Acaris are typically said to have a tendency to gather on dark colors such as black. Thus, if the cardboard sheets are colored black, more Acaris can be collected than in a case where a brightly-colored insect trap can. It is also preferable to use a vegetable ink when coloring the cardboard sheets 2, 3, and 4. If a vegetable ink is used, then chances of letting a coloring ink become a causative substance of soil contamination can be reduced when the insect trap is crushed and buried under soil.

Figure 6:
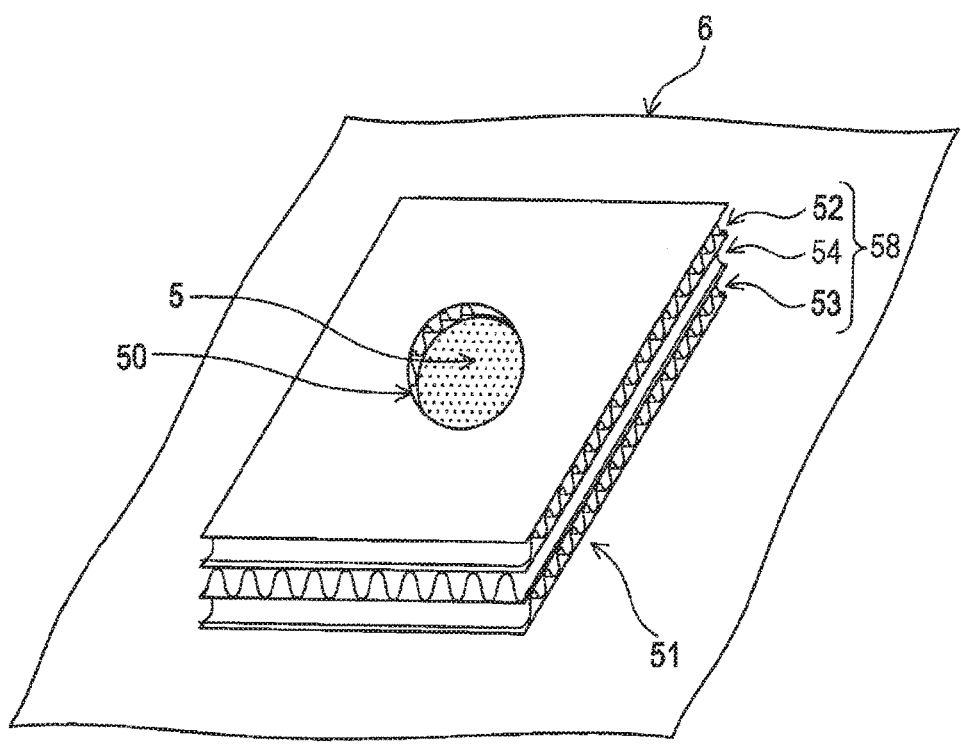
FIG. 6 is a perspective view showing an insect trap according to yet another embodiment.

(3h) As a structure of the insect trap, the aforementioned embodiments showed examples where the exothermic body 5 is housed inside the layered body 8 or inside the layered body 37. Nevertheless, the structure of the insect trap is not limited to the aforementioned examples. For example, an opening may be arranged on the layered body, and a part of the exothermic body may be exposed to the outside from this opening. Specifically, as in an insect trap 51 shown in FIG. 6, a round opening 50 is formed in the central area of a cardboard sheet 52 situated outermost of three cardboard sheets 52, 53, and 54. A part of the exothermic body 5 housed inside the layered body 58 is exposed to the outside of the layered body 58 from the opening 50.

According to the insect trap 51 configured as above, the insect trap 51 can be fixed with a magnet to a specified location. More specifically, the insect trap can be installed on a wall of a cage in the chicken house, for example, by fixing a magnet on the wall and attaching the exposed exothermic body to the magnet.

(3i) A function of one element in the aforementioned embodiments may be separated to several elements, or functions of several elements may be integrated into one element. A part of the configuration of the aforementioned embodiments may be omitted. At least a part of the configuration of one aforementioned embodiment may be added to or replaced with the configuration of another aforementioned embodiment. In addition, any and all modes encompassed in the technical ideas defined only by the words recited in the scope of the claims are the embodiments of the present disclosure.

The invention claimed is:

1. An insect trap comprising:
an exothermic body configured to comprise exothermic powder enclosed in an inner bag that is air permeable, wherein the exothermic powder contains iron powder that releases heat when oxidized; and
a layered body configured with layers of plate-like elements, wherein the layered body comprises gaps as pathways of entry for an insect pest, and wherein a housing space to house the exothermic body is arranged inside the layered body,
wherein the layered body and the inner bag are made of a biodegradable raw material,
wherein the layered body has a layered structure comprising cardboard sheets,
wherein the cardboard sheets have a structure comprising the gaps, which extend parallel to one another,
wherein entries to the gaps are open at an end surface of each of the cardboard sheets, and
wherein the cardboard sheets, adjoining in the layered body, each have a direction of extension of the gaps oriented to be orthogonal to each other when viewed from a layered direction of the cardboard sheets.

2. The insect trap according to claim 1, wherein the layered body carries boric acid.

3. The insect trap according to claim 1, wherein the plate-like elements placed next to one another are bonded with hide glue.

4. The insect trap according to claim 1, wherein the layered body carries an attractant that includes limonene.

5. The insect trap according to claim 1, wherein the inner bag is made of a film material whose base material is cellophane.

6. The insect trap according to claim 1, wherein the layered body is colored in black with a vegetable ink.

7. The insect trap according to claim 1, enclosed in an airtight outer bag.

8. The insect trap according to claim 1,
wherein an opening is formed on the layered body, and
wherein a part of the exothermic body is exposed from the opening.

* * * * *